United States Patent [19]

Braig et al.

[11] Patent Number: 5,288,315
[45] Date of Patent: Feb. 22, 1994

[54] SURFACE COATINGS

[75] Inventors: Adalbert Braig, Weil-Friedlingen, Fed. Rep. of Germany; Emry Phillips, Wakefield, England

[73] Assignee: Ciba-Geigy Corporation, Ardsley, N.Y.

[21] Appl. No.: 808,388

[22] Filed: Dec. 16, 1991

[30] Foreign Application Priority Data

Dec. 20, 1990 [GB] United Kingdom ................. 9027724

[51] Int. Cl.$^5$ ................................. C09D 5/08
[52] U.S. Cl. .............................. 106/14.15; 106/14.16; 106/14.17; 106/14.42
[58] Field of Search ............... 106/14.42, 14.16, 14.15, 106/14.17

[56] References Cited

U.S. PATENT DOCUMENTS 4,151,317 4/1979 Burba et al. .................... 427/388 D
4,784,796 11/1988 Treybig et al. ..................... 252/392

FOREIGN PATENT DOCUMENTS 0410925 1/1991 European Pat. Off. .
1434354 5/1976 United Kingdom .

OTHER PUBLICATIONS

Chem. Abst. (1971) 75, 13236a.
Chem. Abst (1972) 77, 65238 and 65239u.
Derwent Abstract 88-282669, Aug. 1988.
Chem. Abstract 110:156230a, Aug. 1988 (of JP63-207807).

Primary Examiner—Helene Klemanski
Assistant Examiner—Margaret Einsmann
Attorney, Agent, or Firm—William A. Teoli, Jr.; Luther A. R. Hall

[57] ABSTRACT

An aqueous coating composition comprising a) an aqueous film-forming binder; and b) as corrosion inhibitor, a corrosion inhibiting amount of a product produced by reacting i) a mono- or di-aldehyde having the formula I:

$$R-(CHO)_{1\ or\ 2} \qquad I$$

in which R is a $C_1$-$C_{20}$ alkyl or alkylene group, optionally interrupted by one or more O- and/or N-atoms, or substituted by one or more hydroxy or cyano groups, or a $C_6$ or $C_{10}$ aryl or arylene group optionally substituted by one or more $C_1$-$C_{10}$ alkyl groups, $C_1$-$C_{10}$ alkoxy groups, hydroxy or nitro groups, or halogen atoms, with ii) a mono- or di-amine having the formula II:

$$R_1-(NH_2)_{1\ or\ 2} \qquad II$$

in which $R_1$ is a $C_1$-$C_{20}$ alkyl or alkylene group which is optionally interrupted by one or more O- and/or N-atoms, or substituted by one or more hydroxy or cyano groups, a $C_5$-$C_7$ cycloalkyl or cycloalkylene group, a $C_6$ or $C_{10}$ aryl or arylene group or a $C_7$-$C_{12}$ aralkyl or aralkylene group, each of which may be substituted in the cycloalkyl or aryl ring by one or more $C_1$-$C_{10}$ alkyl groups, $C_1$-$C_{10}$ alkoxy groups, hydroxy, nitro groups, or $C_7$-$C_{12}$ aralkyl optionally substituted by an amine group, or halogen atoms.

7 Claims, No Drawings

SURFACE COATINGS

The present invention relates to surface coatings, in particular to coating compositions containing, as corrosion inhibitors, certain Schiff's bases.

When an organic surface coating is applied to a metal substrate, one of the most important requirements of the coating is that it should provide adequate protection against corrosion of the metal substrate. H. Kittel in the article in Lehrbuch der Lacke and Beschichtungen (Textbook of Paints and Coatings), volume V, Stuttgart 1977, 46-103, provides many suggestions as to how coatings can be improved in order to provide better protection for metal substrates.

On the one hand, the barrier function of the coating composition can be improved, in order to keep corrosive agents, e.g. oxygen, water and ions away from the metal surface. As an alternative, it is possible to incorporate into the coating corrosion-inhibiting pigments, which intervene chemically or electrochemically in the corrosion process, e.g. by forming insoluble deposits with corrosion products, or by passivation (polarization) of the metal surface. Metal chromates and lead compounds have been found to be very effective corrosion-inhibiting pigments. To date, much use has been made of metal chromates, particularly because they inhibit both anodic and cathodic corrosion. Nowadays, there are objections to the use of chromates owing to their potential carcinogenic action. Similarly, the use of lead compounds is avoided owing to their chronic toxicity.

The twin factors of environment protection and economy with natural resources are fundamental to any modern chemical manufacture. In the production of surface coatings, these factors have influenced a trend away from expensive, hazardous and polluting hydrocarbon solvent-based surface coatings towards waterborne surface coatings, e.g. electrodepositable aqueous paints.

Recently, there has been an increased commercial interest in the production of surface coatings by electrodeposition, viz the deposition of a film-forming material under the influence of an applied electrical potential. Various coating materials have been developed for this mode of application, but the technique is often accompanied by various disadvantages. In particular, it is difficult to attain desired levels of corrosion inhibition of the metal substrate to be coated, using this method of applying a surface coating.

In GB 1434354, there is disclosed a method of inhibiting the corrosion of steel or aluminium by acidic compounds, by adding to the acidic compound an effective amount of an azomethine, or by pretreating the metal with the azomethine, either neat or as a solution in a solvent, or with its precursors, or by a combination of these methods. Also disclosed are paints, primers and wax or polish compositions containing an azomethine. There is no mention in GB 1434354 that the disclosed paint compositions could be aqueous paints, nor of the use of paints for coating metal substrates which are not to be exposed to acidic conditions.

In Chemical Abstracts 1971, 75, 132360a the corrosion inhibiting properties were examined of the condensation products of aniline with various aliphatic or aromatic aldehydes. All the condensation products effectively inhibited corrosion of steel, ion, nickel and cobalt in 5N HCl at 20° C. and 80° C.

In Chemical Abstracts 1972, 77, 65238t and 65239u, condensation products of various aldehydes with aniline e.g. bispropylidene aniline, are examined as corrosion inhibitors for steel in 5N HCl and 8N $H_2SO_4$.

It is well established, that compounds which are effective as corrosion inhibitors in one environment may not be effective in other media. Thus, for example, in the publication entitled "Peintures, Pigments et Vernis", 1963, 39, 295-303, Chem. Abs. 59, 8974e, it is disclosed that N-heterocycles such as pyrroles, which are known to the excellent corrosion inhibitors in acidic pickling baths, namely the primary use application with which the foregoing prior disclosures are concerned, cause unacceptable yellowing of the coating when formulated in linseed-based paint substrates. Moreover, corrosion inhibitors known to be useful in the treatment of industrial water are usually ineffective in aqueous surface coatings since, due to their high water solubility, they may act as electrolytes in the coating, leading to blistering and de-lamination of the coating.

We have now found certain Schiff's base corrosion inhibitors which impart excellent levels of corrosion inhibition to substrates coated with aqueous surface coating material, especially an aqueous-based electrodepositable coatings system.

Accordingly, the present invention provides an aqueous coating composition comprising a) an aqueous film-forming binder; and b) as corrosion inhibitor, a corrosion-inhibiting amount of a product produced by reacting i) a mono- or di-aldehyde having the formula I

$$R-(CHO)_{1 \text{ or } 2} \qquad \qquad I$$

in which R is a $C_1-C_{20}$ alkyl or alkylene group optionally interrupted by one or more O- and/or N-atoms, or substituted by one or more hydroxy or cyano groups, or a $C_6$ or $C_{10}$ aryl or arylene group optionally substituted by one or more $C_1-C_{10}$ alkyl groups, $C_1-C_{10}$ alkoxy groups, hydroxy, nitro groups or halogen atoms; with ii) a mono- or di-amine having the formula II:

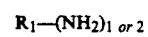
$$R_1-(NH_2)_{1 \text{ or } 2} \qquad \qquad II$$

in which $R_1$ is a $C_1-C_{20}$ alkyl or alkylene group which is optionally interrupted by one or more O- and/or N-atoms or substituted by one or more hydroxy or cyano groups; a $C_5-C_7$ cycloalkyl or cycloalkylene group, a $C_6$ or $C_{10}$ aryl or arylene group or a $C_7-C_{12}$ aralkyl or aralkylene group, each optionally substituted in the cycloalkyl or aryl ring by one or more $C_1-C_{10}$ alkyl groups, $C_1-C_{10}$ alkoxy groups, hydroxy groups, nitro groups, $C_7$ to $C_{12}$ aralkyl groups optionally substituted by an amino group, or halogen atoms.

$C_1-C_{20}$ Alkyl groups R or $R_1$ include methyl, ethyl, n-propyl, isopropyl, n-butyl, t-butyl, n-pentyl, n-hexyl, n-octyl, n-decyl, n-dodecyl, n-tetradecyl, n-hexadecyl, n-octadecyl or n-eicosyl groups. Preferred alkyl groups R or $R_1$ are $C_1-C_6$ alkyl groups. $C_1-C_{20}$ Alkylene groups R or $R_1$ include methylene, ethylene, isopropylene, n-butylene, n-hexylene, n-octylene, n-decylene, n-hexadecylene, n-octadecylene and n-eicosylene groups.

Alkyl groups R or $R_1$ which are interrupted by one or more O- or N-atoms are preferably $C_2-C_6$ alkyl groups interrupted by one or two O- and/or N-atoms e.g. methoxymethyl, ethoxymethyl, 2-methoxyethyl, 2-ethoxyethyl, 3-methoxypropyl, 1- or 2-methoxybutyl, 1-methoxypentyl, 2-methoxy ethoxymethyl or 2-methoxyethyl; methylaminomethyl, ethylaminomethyl, 2-methylaminoethyl, 2-ethylaminoethyl, or 2-methylaminoethylaminomethyl or 2-methylaminoethylaminoethyl. Alkylene groups R or $R_1$ which are interrupted by one or more O- or N-atoms are preferably $C_2$–$C_6$ alkylene groups interrupted by one or two O- and/or N-atoms e.g. 1,2-oxymethylene or a 1,2-aminomethylene group.

Alkyl or alkylene groups R or $R_1$ which are substituted by one or more OH or CN groups are preferably $C_2$–$C_6$ alkyl or alkylene groups substituted by 1OH or CN group e.g. 1-hydroxyethyl, 2- or 3-hydroxypropyl, 1-, 2-, 3- or 4-hydroxybutyl, 1-(1-hydroxy-2-methyl)-propyl or 1-hydroxyhexyl; or 1-cyanoethyl, 2- or 3-cyanopropyl, 1-, 2-, 3- or 4-cyanobutyl, 1-(1-cyano-2-methyl)propyl or 1-cyanohexyl; or 1-hydroxyethylene, 2-hydroxybutylene, 1-cyanoethylene, or 1-cyanohexylene.

$C_5$–$C_7$ Cycloalkyl or cycloalkylene groups $R_1$ are cyclopentyl, cyclohexyl or cycloheptyl groups, or cyclopentylene, cyclohexylene or cycloheptylene groups.

$C_6$- or $C_{10}$-aryl or arylene groups R or $R_1$ are phenyl or naphthyl groups, preferably phenyl groups, or phenylene or naphthylene groups. $C_7$–$C_{12}$ aralkyl or aralkylene groups $R_1$ are preferably benzyl.

Aryl groups R or $R_1$ preferably have the formula III

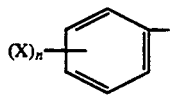

III in which each X is the same or different and is $C_1$–$C_{10}$ preferably $C_1$–$C_4$ alkyl, $C_1$–$C_{10}$ preferably $C_1$–$C_4$ alkoxy, hydroxy, nitro or halogen, preferably chlorine or bromine, and n is 0, 1, 2 or 3.

Examples of aryl groups R or $R_1$ of formula III include phenyl, 4-tolyl, 4-ethylphenyl, 4-n-butylphenyl, 4-methoxyphenyl, 4-ethoxyphenyl, 4-butoxyphenyl, 1- or 4-hydroxyphenyl, 4-hydroxy-3,5-di-t-butylphenyl, 4-nitrophenyl, 1- or 4-chlorophenyl or 1- or 4-bromophenyl.

Preferably, R is a $C_1$–$C_{20}$ alkyl group especially a $C_1$–$C_6$ alkyl group or a phenyl group of formula III; and $R_1$ is preferably a $C_1$–$C_{20}$ alkyl group, especially a $C_1$–$C_6$ alkyl group.

The components b) are not new, and may be obtained e.g. by the reaction of an aldehyde having the formula I

R—(CHO)$_{1 \text{ or } 2}$     I in which R has its previous significance, with an amine of formula II:

$R_1$—(NH$_2$)$_{1 \text{ or } 2}$     II in which $R_1$ has its previous significance.

The composition of the product produced by the reaction between compounds I and II will vary depending on the molar ratios of the respective reactants, and on the functionality of (the number of aldehyde or amine groups, respectively) of the reactants.

For reactions using equimolar amounts of a mono-aldehyde of formula I with a mono-amine of formula II, the reaction product will be, predominantly, a compound having the formula:

R—CH=N—$R_1$     IV in which R and $R_1$ have their previous significance.

For reactions using two moles of a mono-aldehyde of formula I and one mole of a di-amine of formula II, the reaction product will be, predominantly, a compound having the formula V:

[R—CH=N]$_2$$R_1$     V

For reactions using the mole of a di-aldehyde of formula I and one mole of a mono-amine of formula II, the reaction product will be, predominantly, a compound of formula VI:

R—[CH=N—$R_1$]$_2$     VI

When a di-aldehyde of formula I is reacted with a diamine of formula II, the reaction product will be a complex mixture of products comprising e.g. fully-reacted tetra-azomethine products and products containing only one, two or three azomethine linkages, as well as polymeric azomethine products and cyclized products.

It is preferred to react equimolar amounts of mono-aldehydes of formula I with mono-amines of formula II; two moles of a mono-aldehyde of formula I with one mole of a diamine of formula II; or one mole of a di-aldehyde of formula I with two moles of mono-amine of formula II. In these preferred reaction schemes, reaction products are obtained which contain virtually no free primary amino groups or aldehyde groups which could otherwise interfere with the subsequent film-forming processes.

The condensation reaction is conveniently conducted in an organic solvent, in particular in a solvent, e.g. toluene, which forms an azeotropic mixture with water formed during the condensation, thereby facilitating the removal of the water by conventional techniques. The condensation reaction is preferably conducted until the theoretical amount of water has been produced by the condensation reaction.

Examples of reactants of formula I include acetaldehyde, propionaldehyde, butyraldehyde, n-hexanoic aldehyde, n-octanoic aldehyde, n-decanoic aldehyde, n-dodecanoic aldehyde, n-hexadecanoic aldehyde, n-eicosanoic aldehyde; methoxyacetaldehyde, ethoxyacetaldehyde, 4-methoxybutyraldehyde, 12-methoxy-n-decanoic aldehyde, 20-methoxy n-eicosanoic aldehyde; methylaminoacetaldehyde, ethylaminoacetaldehyde; hydroxy-acetaldehyde, 2-hydroxypropionaldehyde, 3-hydroxybutyraldehyde; cyanoacetaldehyde, 2-cyanopropionaldehyde, 3-cyanobutyraldehyde; benzaldehyde, tolualdehyde, anisaldehyde, 2-hydroxybenzaldehyde, 4-nitro-benzaldehyde, 4-hydroxy-3,5-di-t-butylbenzaldehyde; glyoxal, succindialdehyde, adipaldehyde, suberaldehyde; benzene-1,2-dicarboxaldehyde, benzene-1,3-dicarboxaldehyde, benzene-1,4-dicarboxaldehyde.

Examples of reactants of formula II include methylamine, ethylamine, n-propylamine, isopropylamine, n-butylamine, n-hexylamine, n-decylamine, n-hexadecylamine, n-eicosanylamine; methoxymethylamine, ethoxy methylamine, n-butoxymethylamine, ethoxyethylamine, n-butoxyethylamine; methylamino-methylamine, methylaminoethylamine; 2-hydroxy-ethylamine, 3-hydroxypropylamine; 2-cyanoethylamine, 3-cyanopropylamine; cyclopentylamine, cyclohexylamine, cycloheptylamine; aniline, 4-methylaniline, 4-ethylaniline, 4-methoxyaniline, 4-ethoxyaniline, 4-hydroxyaniline, 4-nitroaniline; benzylamine, 4-methylbenzylamine, 4-ethylbenzylamine, 4-hydroxy-benzylamine; 4-nitrobenzylamine; ethylenediamine, 1,3-propylenediamine, 1,4-butylenediamine, 1,5-pentylenediamine, 1,6-hexylenediamine, isophoronediamine, 1,2-phenylene diamine, 1,3-phenylenediamine, 1,4-phenylenediamine, toluene-2,4-diamine, toluene-2,6-diamine, toluene-3,4-diamine, toluene 2,5-diamine, or 4,4$^1$-methylenediamine.

Preferred coating compositions according to the invention are aqueous alkaline paints and aqueous electrocoat paints.

As a component a) the aqueous film-forming binder of the aqueous coating compositions of the present invention, there may be used e.g. an epoxy resin optionally crosslinked with a capped or blocked organic polyisocyanate; acrylic resins optionally and preferably crosslinked with a capped or blocked isocyanate; adducts of epoxy resins with amines, polycarboxylic acids or their anhydrides or aminocarboxylic, mercaptocarboxylic or aminosulphonic acids; polyurethanes; polyesters; and reaction products of phenolic hydroxyl group-containing resins with an aldehyde and an amine or amino- or mercapto- carboxylic or aminosulphonic acid; as well as mixtures of these resins.

Suitable capped or blocked isocyanates include those in which the isocyanate groups have been reacted with a compound so that the resultant capped isocyanate is stable to hydroxyl or amine groups at room temperature, but is reactive with hydroxyl or amine groups at elevated temperatures e.g. from 100° to 300° C.

Any suitable organic polyisocyanate may be used in the production of the blocked organic polyisocyanate e.g. aliphatic compounds e.g. alkylene diisocyanates; aromatic compounds e.g. phenylene diisocyanates; or aliphatic-aromatic diisocyanates e.g. tolylene-or xylylene diisocyanates; triisocyanates e.g. triphenylmethane-4,4,4''-trisocyanate; and tetraisocyanate e.g. 4,4$^1$-diphenyl-dimethylmethane-2,2$^1$-,5,5$^1$-tetraisocyanate.

Any suitable aliphatic, cycloaliphatic, aromatic, alkyl monoalcohol or phenolic compound may be used as a blocking agent in the production of the blocked isocyanates, e.g. methyl alcohol, phenylcarbino or cresol.

Further details of suitable capped or blocked isocyanates, and their production are provided e.g. in U.S. Pat. No. 4,031,050.

Suitable acrylic resins include copolymers of a least one acrylic ester such as an alkyl or hydroxyalkyl acrylate or methacrylate with an ethylenically unsaturated monomer containing a salt-forming group, such as an acrylic monomer containing carboxyl or an amino group and, optionally, another ethylenically unsaturated monomer.

Suitable epoxide resin adducts include those of diglycidyl ethers of dihydric alcohols or bisphenols with a primary or secondary amine, which may be a diamine such as ethylenediamine but is more usually a monoamine such as ethanolamine, 1-amino-2-propanol, deithanolamine or diethylamine, a polycarboxylic acid such as glutaric or adipic acid, a polycarboxylic acid anhydride such as maleic or succinic anhydride, an aminocarboxylic acid such as o-, m- or p-aminobenzoic acid or a mercaptocarboxylic acid. Suitable polyurethanes include adducts of hydroxyl-terminated polyurethanes with polycarboxylic acid anhydrides.

Suitable polyesters include carboxyl-terminated polyesters derived from polyhydric alcohols such as ethylene glycol, 1,2-propylene glycol, 1,3-propylene glycol or butane-1,4-diol with polycarboxylic acids such as glutaric, adipic, maleic, tetrahydrophthalic and phthalic acids or esterifying derivatives thereof.

Suitable reaction products of phenolic hydroxyl-containing resins include reaction products of phenol-terminated adducts of diglycidyl ethers with bisphenols, with aldehydes such as formaldehyde or benzaldehyde and amines such as ethanolamine, diethanolamine or ethylene diamine, aminocarboxylic acids such as glycine, sarcosine or aspartic acid, or mercaptocarboxylic acids such as thioglycolic or mercaptopropionic acid.

The deposited resin film is preferably of an acrylic polymer or of an adduct of an epoxide resin with an amine.

Preferred isocyanate polymers include trimethylene, tetramethylene, m-and p- phenylene, 2,4- or 2,6-tolylene and 4,4- or 1,4-xylylene diisocyanates.

Preferred acrylic polymers include copolymers of at least one monoacrylic monomer containing a carboxyl group and at least one monoacrylic ester, optionally together with at least one other vinyl monomer. Suitable carboxyl-containing monoacrylic monomers from which the copolymers may be derived include acrylic acid, methacrylic acid and adducts of a hydroxyalkyl acrylate or methacrylate with a polycarboxylic acid anhydride. Acrylic and methacrylic acids are particularly preferred carboxyl-containing acrylic monomers.

Suitable monoacrylic esters from which the copolymers may be derived include methyl acrylate, ethyl acrylate, n-butyl acrylate, n-hexyl acrylate, 2-ethylhexyl acrylate and the corresponding methacrylates.

Preferably, at least one monoacrylic ester contains a reactive functional group such as an epoxide group, a primary or secondary amino group, a blocked isocyanate group, or, preferably, a hydroxyl group. Suitable monoacrylic esters having such reactive groups include 2-aminoethyl acrylate, 2-hydroxyethyl acrylate, 2-hydroxypropyl acrylate and the corresponding methacrylates, reaction products of 2-isocyanatoethyl acrylate or 2-isocyanatoethyl methacrylate with an isocyanate-blocking agent, for example as described in U.S. Pat. No. 3,542,739, or reaction products of a polyisocyanate, preferably a tolylene diisocyanate, with a hydroxyalkyl acrylate or methacrylate such as those hereinbefore described an isocyanate-blocking agent, for example as described in U.S. Pat. No. 4,113,958. Isocyanate-blocking agents are well known and include alcohols, phenols, mercaptans, primary and secondary amines, oximes, triazoles, pyrazoles and lactams. Preferred such blocking agents are oximes and lactams. A particularly preferred reactive group-containing monoacrylic ester is 2-hydroxyethyl methacrylate.

The optional vinyl monomer which may be copolymerised with the carboxyl-containing acrylic monomer and the monoacrylic ester may be, for example, a vinyl ester such as vinyl acetate, a vinyl halide such as vinyl chloride or, preferably, a styrene, such as styrene itself, alpha-methylstyrene or p-chlorostyrene, styrene itself being particularly preferred.

Other preferred acrylic polymers include copolymers of at least one monoacrylic monomer containing a tertiary amine group and at least one monoacrylic ester having a reactive functional group, optionally together with at least one other vinyl monomer. Suitable monoacrylic monomers containing a tertiary amine group from which the copolymers may be derived include dialkylaminoalkyl acrylates and dialkylaminoalkyl methacrylates, preferably 2-(dimethylamino)ethyl acrylate, 2-(diethylamino)ethyl acrylate, 2-(dimethylamino) propyl acrylate and the corresponding methacrylates, 2-(dimethyl-amino)ethyl methacrylate being especially preferred. Reactive group-containing monoacrylic esters copolymerised with the tertiary amine-containing monoacrylic monomer may be acrylates or methacrylates containing an epoxide group, a blocked isocyanate group or, preferably a hydroxyl group, as hereinbefore described for the reaction group-containing monoacrylic esters copolymerised with the carboxyl-containing monoacrylic monomer.

The optional vinyl monomer which may be copolymerised with the tertiary amine group-containing monoacrylic monomer and the reactive group-containing monoacrylic ester may be, for example, an alkyl acrylate or methacrylate, such as methyl acrylate, ethyl acrylate, n-butyl acrylate, 2-ethylhexyl acrylate and the corresponding methacrylates, a vinyl ester such as vinyl acetate, a vinyl halide such as vinyl chloride or a styrene such as styrene, alpha-methyl styrene or p-chlorostyrene. Amongst these, the alkyl acrylates and methacrylates and styrene are preferred.

Particularly preferred acrylic polymers for use in the method of the invention are copolymers of (a) acrylic acid, methacrylic acid or 2-(dimethylamino)ethyl methacrylate with b) a hydroxyalkyl acrylate or methacrylate and, optionally, (c) at least one further vinyl monomer, preferably selected from alkyl acrylates, alkyl methacrylates, styrene and mixtures of two or more thereof. The acrylates and methacrylates (b) and the alkyl acrylates and methacrylates for (c) are as hereinbefore described, with 2-hydroxyethyl methacrylate being particularly preferred as (b) and a mixture of styrene and 2-ethylhexyl acrylate being particularly preferred as (c).

The acrylic polymers may be prepared by conventional polymerisation processes using free radical polymerisation initiators such as peroxides or azo compounds, usually to give polymers having a number average molecular weight of 5000 or more, preferably 5000 to 50,000. Thus the monomers may be heated with the initiator in solution in an organic solvent, preferably a solvent which is miscible with the medium from which the polymer is to be electrodeposited. Conventional chain transfer agents such as tert.dodecyl mercaptan can be used when desired.

Preferred adducts of an epoxide resin with an amine are adducts of a polyglycidyl ether, which may be of a polyhydric phenol or a polyhydric alcohol, with a monoamine. Suitable polyglycidyl ethers include those of dihydric alcohols such as butane-1,4-diol, neopentyl glycol, hexamethylene glycol, oxyalkylene glycols and polyoxyalkylene glycols, and trihydric alcohols such as glycerol, 1,1, 1-trimethylolpropane and adducts of these alcohols with ethylene oxide or propylene oxide. It will be understood by those skilled in the art that these polyglycidyl ethers or polyhydric alcohols are usually advanced, i.e. converted into longer chain higher molecular weight polyglycidyl ethers, for example by reaction with a dihydric alcohols or phenol, so that the resulting polyglycidyl ethers give adducts with suitable electrodepositable film-forming properties on reaction with the secondary monoamine. Preferred polyglycidyl ethers are those of polyhydric phenols, including bisphenols such as bisphenol F, bisphenol A and tetrabromobisphenol A and phenolic novalak resins such as phenol-formaldehyde or cresol-formaldehyde novolak resins. These polyglycidyl ethers of phenols may have been advanced, for example by reaction with dihydric alcohols or phenols such as those hereinbefore described. Particularly preferred polyglycidyl ethers are polyglycidyl ethers of bisphenol A advanced by reaction with bisphenol A.

Monoamines suitable for adduct formation with the polyglycidyl ethers include primary, secondary or tertiary amines. Secondary amines are preferred e.g. dialkylamines such as diethylamine, di-n-propylamine, di-isopropylamine, di-n-butylamine, di-n-octylamine and di-n-dodecylamine or nitrogen heterocycles such as piperidine or morpholine.

Preferred secondary monoamines are secondary alkanolamines such as diethanolamine, N-methylethanolamine, N-butylethanol-amine, diisopropanolamine, N-methylisopropanolamine or di-n-butanolamine. A particular preferred secondary alkanolamine is diethanolamine.

Thus preferred adducts of polyglycidyl ether with a secondary monamine are adducts of a polyglycidyl ether of a polyhydric phenol, which may have been advanced, with a secondary alkanolamine, while particularly preferred such adducts are those of a polyglycidyl ether of bisphenol A, advanced by reaction with bisphenol A, with diethanolamine.

If the organic resin is to be applied by electrodeposition, this may be carried out using conventional procedures.

Thus the electrodepositable resin, optionally together with conventional additives such as pigments, dyes, extenders, light stabilizers, antioxidants, further corrosion inhibitors, dispersing aids, curing catalysts, flow control agents, thixotropic agents, adhesion promoters, fillers and plasticizers, can be dissolved or dispersed in an aqueous medium, which may contain a minor amount of an organic solvent, together with an acid to at least partially neutralise salt-forming groups on the resin. The aqueous electrodeposition medium generally contains from 2 to 60%, preferably from 5 to 25%, by weight of the resin. The pigments can be organic, inorganic or metallic pigments, for example titanium dioxide, iron oxide, aluminium bronze, phthalocyanine blue etc. It is also possible to use concomitantly anti-corrosion pigments, for example pigments containing phosphates or borates, metal pigments and metal oxide pigments (see Farbe and Lack 88 (1982)), 183) or the pigments described in EP-A-54,267.

Examples of extenders which can be used concomitantly are talc, alumina, aluminium silicate, baryte, mica or silica. If desired, the corrosion inhibitor can be applied to a neutral carrier. Suitable carriers are, in particular, pulverulent extenders or pigments. This technique is described in greater detail in German Offenlegungsschrift 3,122,907.

In addition to the component b), the coating composition can also contain another organic, metal-organic or inorganic corrosion inhibitors, for example salts of nitroisophthalic acid, tannin, phosphoric esters, technical amines, substituted benztriazoles or substituted phenols, such as are described in German Offenlegungsschrift 3,146,265.

The corrosion inhibitor component b) may be added to the electrodepositable coating system during the preparation of the latter, for example, during the distribution of the pigment by grinding e.g. by the methods disclosed in EP 107089. Alternatively, the corrosion inhibitors can be incorporated into the non-emulsified resins and also into the grind resin. The corrosion inhibitors are preferably used in an amount of 0.01 to 20% by weight, preferably 0.05 to 5% by weight, based on the solids content of the electrodepositable coating composition.

Electrodeposition for only a few minutes, usually one minute, at a voltage of up to 500 volts is sufficient in most cases. Voltages as low as 2 volts may be used in some cases, especially when the size of the electrode on which the resin film is deposited is small in relation to the other electrode. For example, a cathodically depositable resin may be deposited on a small cathode in a tank where the whole of the tank is the anode, at voltages of 2 volts or 5 volts. Adhesion of the resin film may be improved if it is deposited in a stepwise fashion, first at a low voltage and then at a higher voltage. For example, a good coating can be obtained by electrodepositing the resin at 2 volts for 2 minutes, followed by deposition at 5 volts for up to 5 minutes. The coating compositions of the present invention may be applied to any electrically conductive substrate especially metals such as iron; steel; e.g. cold-rolled steel, optionally treated with zinc phosphate or galvanized; copper, zinc; and aluminium; more especially zinc or aluminium alloys.

After electrodeposition of the organic film, the substrate is rinsed in de-mineralized water, dried and baked at elevated temperatures e.g. up to 260° C.

The following Examples further illustrate the present invention.

EXAMPLE 1

Preparation of
N,N$^1$-Bis(4$^1$-methylbenzylidene)-1,6-hexane diamine

Tolualdehyde (24.03 g, 0.2 mole) is carefully added to a solution of 1,6-hexanediamine (11.62 g, 0.1 mole) in toluene (200 ml). A slight exotherm to 30° C. is observed. The resulting solution is heated at reflux until water (2.8 ml) is evolved. Evaporation of the solution gives 29.3 g (87%) of a pale pink solid having a melting point of 76° to 78° C.

Elemental analysis

Theory for $C_{22}H_{28}N_2$ C, 82.5; H, 8.75; N, 8.75%. Found C, 82.4; H, 8.9; N, 8.4%.

EXAMPLE 2 to 9

Using the procedure set out in Example 1, but changing the respective starting materials, the compounds indicated in the following Table are obtained:

TABLE 1

| Example | Aldehyde | Amine | Molar Ratio Aldehyde to Amine | Physical Properties | Elemental Analysis |
|---|---|---|---|---|---|
| 2 | p-OHC-C$_6$H$_4$-CHO | nC$_4$H$_9$NH$_2$ | 1:2 | Brown Oil | Theory C, 82.2; H, 8.2 N, 9.9% Found C, 8.3; H, 8.5; N, 9.5% |
| 3 | C$_6$H$_5$-CHO | H$_2$N(CH$_2$)$_6$NH$_2$ | 2:1 | Brown Oil | Theory C, 82.2; H, 8.2 N, 9.6% Found C, 81.3; H, 8.5; N, 9.9% |
| 4 | C$_6$H$_5$-CHO | H$_2$N(CH$_2$)$_2$NH$_2$ | 2:1 | Brown Oil | Theory C, 81.4; H, 6.8; N, 11.9% Found C, 79.8; H, 6.9; N, 11.7% |
| 5 | C$_3$H$_7$CHO | H$_2$N(CH$_2$)$_5$CN | 1:1 | Brown Oil | Theory C, 73.2; H, 9.8; N, 17.4% Found C, 73.1; H, 10.1 N, 17.4% |
| 6 | C$_6$H$_{13}$CHO | H$_2$N(CH$_2$)$_4$NH$_2$ | 2:1 | Brown Oil | Theory C, 77.1; H, 12.9 N, 10.0% Actual C, 75.5; H, 12.9 N, 9.7% |
| 7 | 2,6-di-tBu-4-CHO-phenol | H$_2$N(CH$_2$)$_6$NH$_2$ | 2:1 | M.P. 172-3° C. | Theory C, 78.8; H, 10.2 N, 5.1% Found C, 77.8; H, 9.8; N, 5.0% |

TABLE 1-continued

| Example | Aldehyde | Amine | Molar ratio Aldehyde | Analysis |
|---|---|---|---|---|
| 8 | 2-hydroxybenzaldehyde (salicylaldehyde: CHO, OH on benzene) | H₂N(CH₂)₂NH₂ | 2:1 | M.P. 121-2° C. Theory C, 71.6; H, 6.0; N, 10.4% Found C, 71.7; H, 6.01; N, 10.6% |
| 9 | 4-methoxybenzaldehyde (CHO, OCH₃ on benzene) | H₂N(CH₂)₆NH₂ | 2:1 | M.P. 72-3° C. Theory C, 75.0; H, 8.0; N, 8.0% Found C, 74.6; H, 8.1; N, 8.1% |

| Example | Aldehyde | Amine | Molar ratio Aldehyde | Analysis |
|---|---|---|---|---|
| 10 | 4-chlorobenzaldehyde (CHO, Cl on benzene) | H₂N(CH₂)₆NH₂ | 2:1 | m.p. 78-9° C. ¹HNMR(CDCl₃) δ1.50(8H); δ3.56(4H); δ7.50(8H); δ8.18(2H). |
| 11 | terephthalaldehyde (1,4-diCHO benzene) | cyclohexylamine (C₆H₁₁-NH₂) | 1:2 | m.p. 128-130° C. ¹HNMR(CDCl₃) δ1.52(20H); δ3.02(2H); δ7.6(4H); δ8.15(2H) |
| 12 | 4-(2-phenylvinyl)benzaldehyde (CHO-C₆H₄-CH=CH-C₆H₅) | cyclohexylamine | 1:1 | m.p. 139-141° C. ¹HNMR(CDCl₃) δ1.4(10H); δ2.94(1H); δ7.2(11H); δ8.0(1H) |
| 13 | benzaldehyde (C₆H₅-CHO) | cyclohexylamine | 1:1 | B.P. 75-80° C./0.1 mm ¹HNMR(CDCl₃) δ1.5(10H); δ3.3(1H); δ7.6(5H); δ3.2(1H) |

EXAMPLES 14-21

An aqueous alkaline paint formulation having a solids content of 56.15 wt % is prepared using the following formulation:

60.03 wt % Bayhydrol B (30% in water);
0.14 wt % Servosyn WEB (8%);
0.28 wt % Ascinin;
18.18 wt % Bayferrox 130M;
5.15 wt % Heladol 10;
10.6 wt % Micronised talc;
0.2 wt % Aerosil 300;
1.06 wt % ZnO;
0.9 wt % butylglycol;
0.005 wt % aluminium octoate; and
0.46 wt % water 1.12 wt % (2% by weight on solids content) of each of the products of Examples 1 to 8 is dispersed in separate samples of the paint formulation.

Each paint sample is applied on to coldroll tested plates at a layer thickness of 55 to 60 microns, and dried for 72 hours at 20° C. A scribe (70×0.5 mm) is applied as a defined damage of the coating. The painted plates are subjected to a salt spray procedure (168 hours) as specified in ASTMB117. At the end of the test, the coating is removed by treatment with concentrated sodium hydroxide solution, and the corrosion of the metal at the cross-cut (as specified in DIN 53, 167) and over the remainder of the surface is assessed. In each case, the assessment is carried out in accordance with a 6-point scale. The sum of the assessment of the coating and the assessment of the metal, gives the anti-corrosion value AC. The higher the figure AC, the more effective is the inhibitor tested.

The results of the salt spray test are summarised in Table 2.

TABLE 2

| Example | Corrosion Inhibitor | Amount Added | Assessment of Coating | Assessment of Metal | AC |
|---|---|---|---|---|---|
| — | None | — | 2.2 | 0.6 | 2.8 |
| 14 | Product of Example 1 | 2% | 3.2 | 0.6 | 3.8 |
| 15 | Product of Example 2 | 2% | 2.6 | 2.8 | 5.4 |
| 16 | Product of Example 3 | 1% | 3.8 | 4.2 | 8.0 |
| 17 | Product of Example 4 | 2% | 2.0 | 1.7 | 3.7 |
| 18 | Product of Example 5 | 1% | 3.2 | 1.7 | 4.9 |
| 19 | Product of Example 6 | 1% | 3.4 | 1.7 | 5.1 |
| 20 | Product of Example 7 | 1% | 3.4 | 0.6 | 4.0 |
| 21 | Product of Example 8 | 2% | 1.6 | 1.7 | 3.3 |

It can be seen that the products of Examples 1 to 8 are highly effective corrosion inhibitors, as indicated by the AC values.

EXAMPLE 22 AND 31

An electrodip coating is prepared as follows. 507.2 g of a two-component lacquer (33.5% solids), based on an amine-modified epoxide resin and a blocked diisocyanate, are mixed with 3.5 g of propylene glycol monophenylether, 17.6 g of lactic acid, 3.5 g of a nonionic detergent and 9 g of the corrosion inhibitor under test and listed in Table 3 below. The mixture is homogenised by stirring and, under rapid stirring, 468 g water are slowly added in three portions. The resulting emulsion has a pH of 4.9 and a solids content of 18%.

To 430 g of this emulsion are added 95 g of a grey pigment paste (containing carbon black, titanium dioxide and aluminium silicate), under stirring. Finally 475 g of water are slowly added. This bath has a solids content of 20% and a pH of 5.2. The concentration of the corrosion inhibitor is 4 g/l, or 2% related to the solids.

The coating is electrodeposited on cold-rolled steel plates (7.5×15 cm) which are zinc phosphated by Chemohos® 168 (Chemfil Corp). The deposition is carried out at a temperature of 29° C. and a voltage of 200 v for 2 minutes. Afterwards, the plates are rinsed with water, dried by an air-stream and baked 30 minutes a) at 176° C. and b) at 163° C. The resulting coatings have a thickness of approximately 25 microns.

The coated films are cut with a Bonder 205 cutting device (cut is 70×0.5 mm). The plates are tested in a four week test according to the General Motors Test Method TM 54-56. This comes in the first week of a daily cycle of 15 minutes immersion in a 5% NaCl solution, 75 minutes storing at room temperature and 22.5 hours in a vapour chamber at 60° C. and 85% relative humidity. After five cycles, the samples are stored for 2 days in the vapour chamber at 60° C./85% relative humidity.

The daily cycle in the second, third and fourth week is 1 hour dry storing at 60° C., 30 minutes storing at −23° C., 15 minutes immersion in 5% NaCl solution, 75 minutes storing at room temperature and 21.5 hours in the vapour chamber at 60° C./85% relative humidity.

After five cycles the samples are stored for two days in the vapour chamber at 60° C./85% relative humidity.

After four weeks testing, the samples are rinsed with warm water, and the parts of the lacquer which no longer adhere to the metal are scratched off. The width of the corroded zone is shown in Table 3.

TABLE 3

| Example | Corrosion Inhibitor | Amount Added | Bake Temperature | Width of corrosion zone (mm) |
|---|---|---|---|---|
| — | None | — | 176° C. | >35 |
| 22 | Product of Example 1 | 2% | 176° C. | 20 |
| 23 | Product of Example 2 | 2% | 176° C. | 0–1 |
| — | None | — | 163° C. | Infinite (severe rust) |
| 24 | Product of Example 1 | 2% | 163° C. | 20 |
| 25 | Product of Example 2 | 2% | 163° C. | 30 |

| Example | Corrosion Inhibitor | Amount Added | Bake Temperature | Corrosion Zone Scribe (mm) | Corrosion Zone Edge (mm) |
|---|---|---|---|---|---|
| Blank | None | — | 171 | 10 | 12 |
| 26 | Product of Example 10 | 2% | 171 | 6 | 6 |
| 27 | Product of Example 11 | 2% | 171 | 10 | 10 |
| 28 | Product of Example 13 | 2% | 171 | 6 | 8 |
| Blank | None | — | 160 | Fail | Fail |
| 29 | Product of Example 10 | 2% | 160 | 9 | 9 |
| 30 | Product of Example 11 | 2% | 160 | 20 | 9 |
| 31 | Product of Example 13 | 2% | 160 | 9 | 6 |

EXAMPLES 32 TO 34

The procedure described in Examples 22 to 31 is repeated except that steel plates are used which are zinc phosphated with Bonderite 925 (Parker Chem. Co.) The results obtained are summarised in Table 4.

TABLE 4

| Example | Corrosion Inhibitor | Amount Added | Bake Temperature | Width of corrosion zone (mm) |
|---|---|---|---|---|
| — | None | — | 176° C. | >25 |
| 32 | Product of Example 2 | 2% | 176° C. | 0–1 |
| — | None | — | 163° C. | >35 |
| 33 | Product of Example 1 | 2% | 163° C. | 16–17 |
| 34 | Product of Example 2 | 2% | 163° C. | 9–10 |

We claim:

1. An aqueous electrodepositable or alkaline paint composition comprising a) an aqueous film-forming binder; and b) as corrosion inhibitor, a corrosion inhibiting amount of a product produced by reacting i) a mono- or di-aldehyde having the formula I:

$$R\text{—}(CHO)_{1 \text{ or } 2} \qquad \qquad I$$

in which R is a $C_1$-$C_{20}$alkyl or alkylene group, optionally interrupted by one or more O- and/or N-atoms, or substituted by one or more hydroxy or cyano groups, or a $C_6$ or $C_{10}$ aryl or arylene group optionally substituted by one or more $C_1$-$C_{10}$alkyl groups, $C_1$-$C_{10}$alkoxy groups, hydroxy or nitro groups, or halogen atoms, with ii) a mono- or di-amine having the formula II:

   II in which $R_1$ is a $C_1$-$C_{20}$alkyl or alkylene group which is optionally interrupted by one or more O- and/or N-atoms, or substituted by one or more hydroxy or cyano groups, a $C_5$-$C_7$cycloalkyl or cycloalkylene group, a $C_6$ or $C_{10}$aryl or arylene group or a $C_7$-$C_{12}$aralkyl or aralkylene group, each of which may be substituted in the cycloalkyl or aryl ring by one or more $C_1$-$C_{10}$alkyl groups, $C_1$-$C_{10}$alkoxy groups, hydroxy, nitro group, or $C_7$-$C_{12}$aralkyl optionally substituted by an amine group, or halogen atoms.

2. A composition according to claim 1 in which R is a $C_1$-$C_{20}$ alkyl group or a group of formula III:

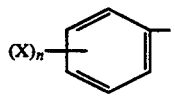   III in which each X is the same or different and is $C_1$-$C_{10}$ alkyl, $C_1$-$C_{10}$ alkoxy, hydroxy, nitro or halogen, and n is 0, 1, 2 or 3; and $R_1$ is $C_1$-$C_{20}$ alkyl.

3. A composition according to claim 2 in which X is $C_1$-$C_4$ alkyl, $C_1$-$C_4$ alkoxy, hydroxy, nitro, chlorine or bromine; and $R_1$ is $C_1$-$C_6$ alkyl.

4. A composition according to claim 1 in which the aqueous film-forming binder, component a), is an epoxy resin, optionally crosslinked with a capped or blocked organic polyisocyanate; an acrylic resin, optionally crosslinked with a capped or blocked isocyanate; an adduct of an epoxy resin with an amine, polycarboxylic acid or its anhydride, or amino carboxylic acid mercaptocarboxylic acid or amino sulphonic acid; a polyurethane; a polyester; or a reaction product of a phenolic hydroxyl group-containing resin with an aldehyde and an amine or amino- or mercapto-carboxylic aminosulphonic acid; or a mixture of these.

5. A composition according to claim 1 in which one or more of a pigment, dye, extender, a flow control auxiliary, dispersing agent, thixotropic agent, adhesion promoter, antioxidant, light stabilizer and a curing catalyst are also present.

6. A composition according to claim 1 in which the corrosion inhibitor b) is present in amount of from 0.01 to 20% by weight, based on the solids content of the paint composition.

7. A composition according to claim 6 in which the corrosion inhibitor b) is present in amount of from 0.5 to 5% by weight, based on the solids content of the paint composition.

* * * * *